(12) United States Patent
Van Oort et al.

(10) Patent No.: US 8,757,435 B2
(45) Date of Patent: Jun. 24, 2014

(54) METHOD, SYSTEM AND DEVICE FOR ASSISTING A PATIENT IN COMPLYING WITH A MEDICAL REGIME

(75) Inventors: Andreas Bernardus Petrus Van Oort, Tilburg (NL); Marlies Van Dullemen, Leiden (NL); Noor Doucet-Liem, Leiden (NL); Annemieke Westerink, Rotterdam (NL); Erwin Christiaan Alexander Van Der Star, Tilburg (NL)

(73) Assignee: Vitaphone Nederland B.V., Tilburg (NL)

( * ) Notice: Subject to any disclaimer, the term of this patent is extended or adjusted under 35 U.S.C. 154(b) by 1269 days.

(21) Appl. No.: 12/180,059

(22) Filed: Jul. 25, 2008

(65) Prior Publication Data

US 2009/0030730 A1     Jan. 29, 2009

(30) Foreign Application Priority Data

Jul. 26, 2007  (EP) .................................. 07113285

(51) Int. Cl.
*B65H 1/00*         (2006.01)
(52) U.S. Cl.
USPC ................. 221/197; 221/30; 221/69; 221/70; 221/71; 221/74; 700/244; 700/236
(58) Field of Classification Search
USPC ........... 340/573.1, 7.3; 700/244, 236; 221/25, 221/3, 30, 69, 70, 71, 74, 197
See application file for complete search history.

(56) References Cited

U.S. PATENT DOCUMENTS

| | | | |
|---|---|---|---|
| 3,367,535 A | 2/1968 | Tanguay | |
| 4,797,283 A | 1/1989 | Allen et al. | |
| 5,102,008 A * | 4/1992 | Kaufman et al. | 221/25 |
| 5,623,242 A * | 4/1997 | Dawson et al. | 340/7.3 |
| 6,150,942 A * | 11/2000 | O'Brien | 340/573.1 |
| 6,961,285 B2 * | 11/2005 | Niemiec et al. | 368/10 |
| 8,019,471 B2 * | 9/2011 | Bogash et al. | 700/242 |
| 2001/0028308 A1 * | 10/2001 | De La Huerga | 340/573.1 |
| 2002/0080034 A1 | 6/2002 | Yahalom | |

(Continued)

FOREIGN PATENT DOCUMENTS

| | | |
|---|---|---|
| DE | 19835940 A1 | 2/2000 |
| DE | 19835941 A1 | 2/2000 |
| WO | WO 01/93801 | 12/2001 |
| WO | WO 02078595 | 10/2002 |

OTHER PUBLICATIONS

Official Search Report of the European Patent Office in counterpart foreign application No. EP 07113285.6 filed Jul. 26, 2007.

*Primary Examiner* — Lena Najarian
*Assistant Examiner* — Natalie A Pass
(74) *Attorney, Agent, or Firm* — Steven M. Koehler; Westman, Champlin & Koehler, P.A.

(57) ABSTRACT

The invention relates to a method, system and dispensing device for assisting a patient in complying with a medical regimen. The system includes an electronic dispensing device to be used by the patient which comprises a device to obtain information about the regimen. A device registers operation of the dispensing device by the patient taking the medicines. A warning device reminds a patient of the regimen. A medicine packing station packs the medicine within a package in portions to be taken according to the regimen. A database stores information about the regimen. A service center is provided to assist when necessary. A communication network is provided for communication between the dispensing device and the service center and/or between the service center and the patient.

14 Claims, 9 Drawing Sheets

(56) References Cited

U.S. PATENT DOCUMENTS

| | | |
|---|---|---|
| 2003/0099158 A1 | 5/2003 | De La Huerga |
| 2004/0039481 A1 | 2/2004 | De La Huerga |
| 2004/0172162 A1 | 9/2004 | Bonney et al. |
| 2005/0177275 A1 | 8/2005 | Harvey et al. |
| 2005/0268909 A1* | 12/2005 | Bonney et al. ........... 128/203.15 |
| 2006/0124655 A1* | 6/2006 | Ratnakar ........................... 221/3 |
| 2006/0237002 A1 | 10/2006 | Bonney et al. |
| 2007/0185615 A1* | 8/2007 | Bossi et al. ................... 700/244 |

\* cited by examiner

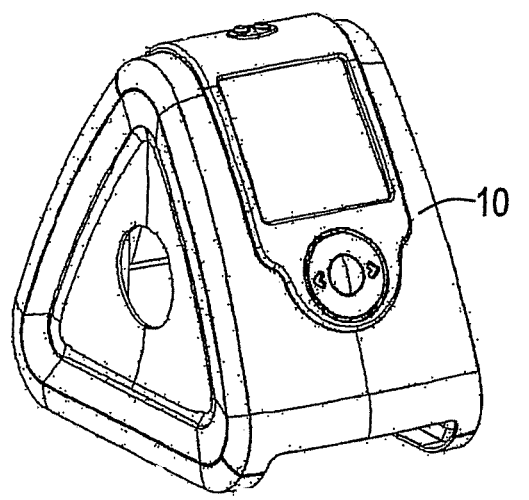
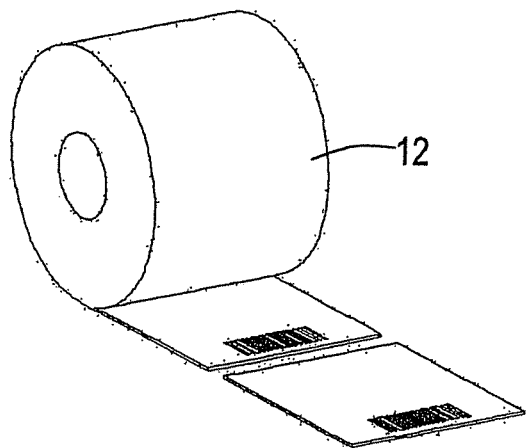
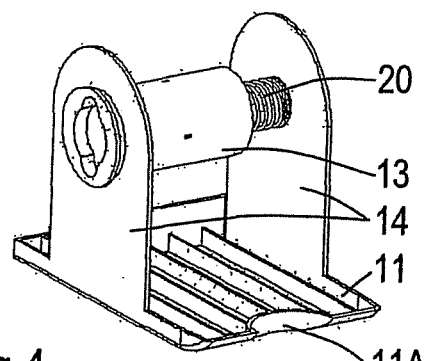
Fig.4

METHOD, SYSTEM AND DEVICE FOR ASSISTING A PATIENT IN COMPLYING WITH A MEDICAL REGIME

BACKGROUND

The discussion below is merely provided for general background information and is not intended to be used as an aid in determining the scope of the claimed subject matter.

Aspects of the present invention relate to a method, system and device for assisting a patient to comply with a medical regimen. Several methods, systems and devices are known in the art and they are all aiming at an improvement of the quality of life of patients by simplifying the compliance by reminding or warning patients when medicines should be taken and by supplying dispensing devices that are simple to operate.

SUMMARY

This Summary and Abstract are provided to introduce some concepts in a simplified form that are further described below in the Detailed Description. This Summary and Abstract are not intended to identify key features or essential features of the claimed subject matter, nor are they intended to be used as an aid in determining the scope of the claimed subject matter. In addition, the description herein provided and the claimed subject matter should not be interpreted as being directed to addressing any of the short-comings discussed in the Background.

The method and system herein described enables a patient to comply with the regimen by providing a service center which is able to communicate with at least the dispensing device and the patient, but preferably also with a pharmacy, medical doctor(s) and/or a medicine packing station.

The device according to an aspect of the invention is very safe and simple to operate and it minimizes the handling when filling it with medicines, especially if the medicine package, a holding element and a housing part of the dispensing device are exchangeable as a unit, because this would eliminate the chance of failures during the action of filling the dispensing device with a new medicine package.

In one embodiment, the device leads to a medicine package which is safe and easy to handle before, during and after use the dispensing device and allows the dispensing device to be kept simple for dispensing the medicine portions in the package. The drive for the spindle can be used to dispense the medicine containers, in particular bags of the medicine package, but in case the dispensing takes place completely manually, particularly by pulling out the strip of bags through the outlet opening of the dispensing device, the drive can be used to wind the strip of bags back on the spindle again if the patient has pulled too many bags out of the dispensing device. This prevents misinformation of the dispensing device which could lead to incorrect warning signals.

In a further embodiment, The drive for the spindle can be a gripping part, such as finger grips, connected to the spindle to manually rotate the spindle. This feature can lead to a simple and stable device with clear visual and tactile feedback and as a further advantage that the bottom can easily be used as an integral counter-surface for a clamping member. This can easily be operated with one hand or arm while the other hand is used to separate a medicine container from the medicine package. The clamping member can be a separate part, but it can also be integrated in the upper housing part which is movable, in particular pivotable with respect to the bottom. Of course it would also be possible that two other housing parts are movable with respect to each other to operate the clamping member.

In yet a further embodiment, the upper part of the housing is pivotable with respect to the bottom, and the bottom includes a support member supporting the upper housing part in a pivotal manner. This leads to the advantage that the spindle can be manually disengaged with minimum handling actions from the upper housing part as only one push button requires actuation instead of two push buttons on both ends of the spindle, which would require more efforts and complicated handling from the patient. Of course, also if the holding element would be differently configured, for example as a box containing a medicine package, such as a strip, the latter feature will also be conceivable.

BRIEF DESCRIPTION OF THE FIGURES

Further features and advantages of the invention will be described hereafter with reference to the drawings showing embodiments of the invention by way of example only.

FIG. 4 is an exploded perspective view corresponding to that of FIG. 2 but also showing the medicine package and holding element separately.

DETAILED DESCRIPTION OF ILLUSTRATIVE EMBODIMENTS

Figure 1:
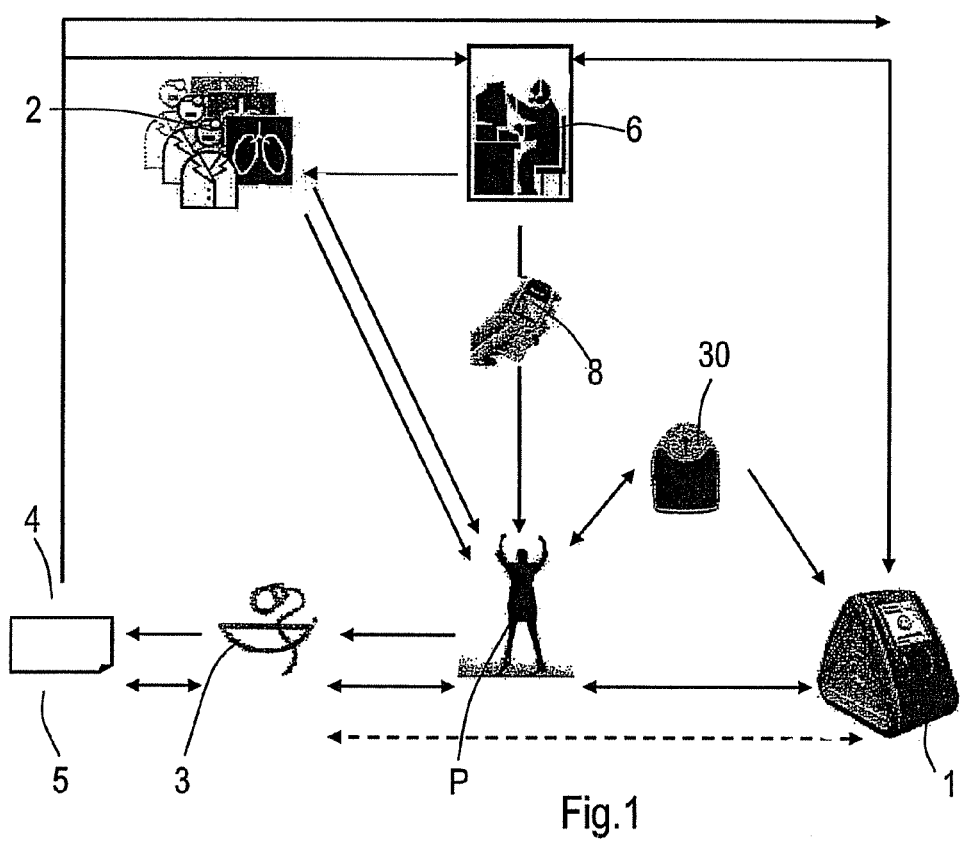
FIG. 1 very schematically illustrates an embodiment of a system for assisting a patient in complying with a medical regimen.
Figure 2:
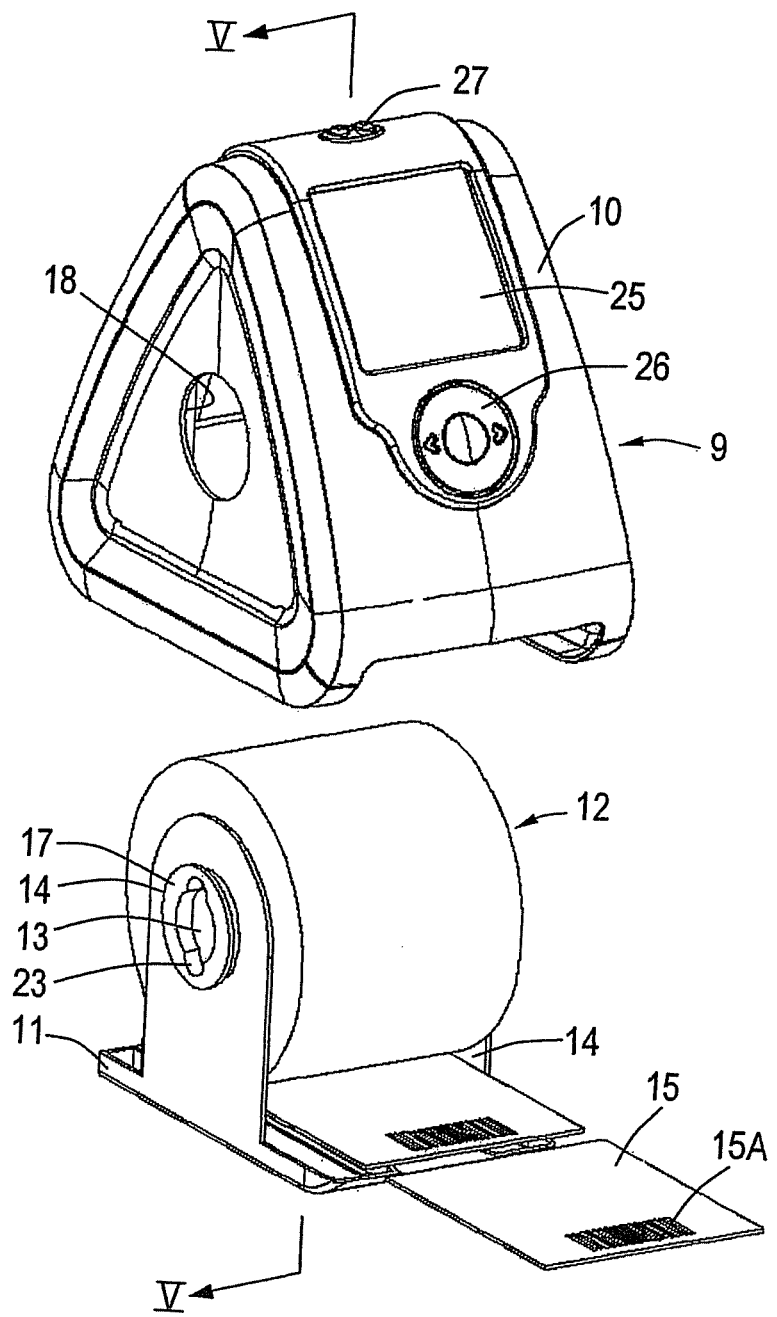
FIG. 2 is an exploded view of an embodiment of the device for storing and dispensing medicines, which may be used in the system as shown in FIG. 1.
Figure 3:
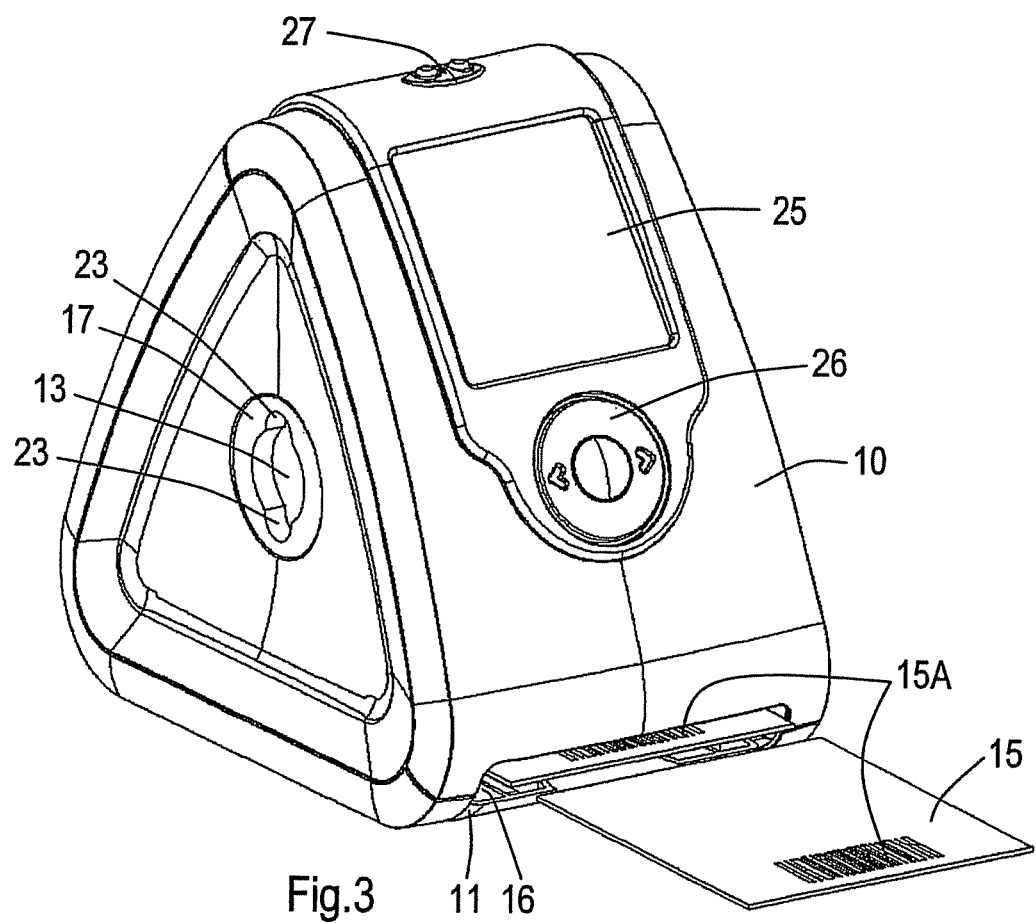
FIG. 3 is a perspective view similar to that of FIG. 2 but showing the device in mounted condition.
Figure 5:
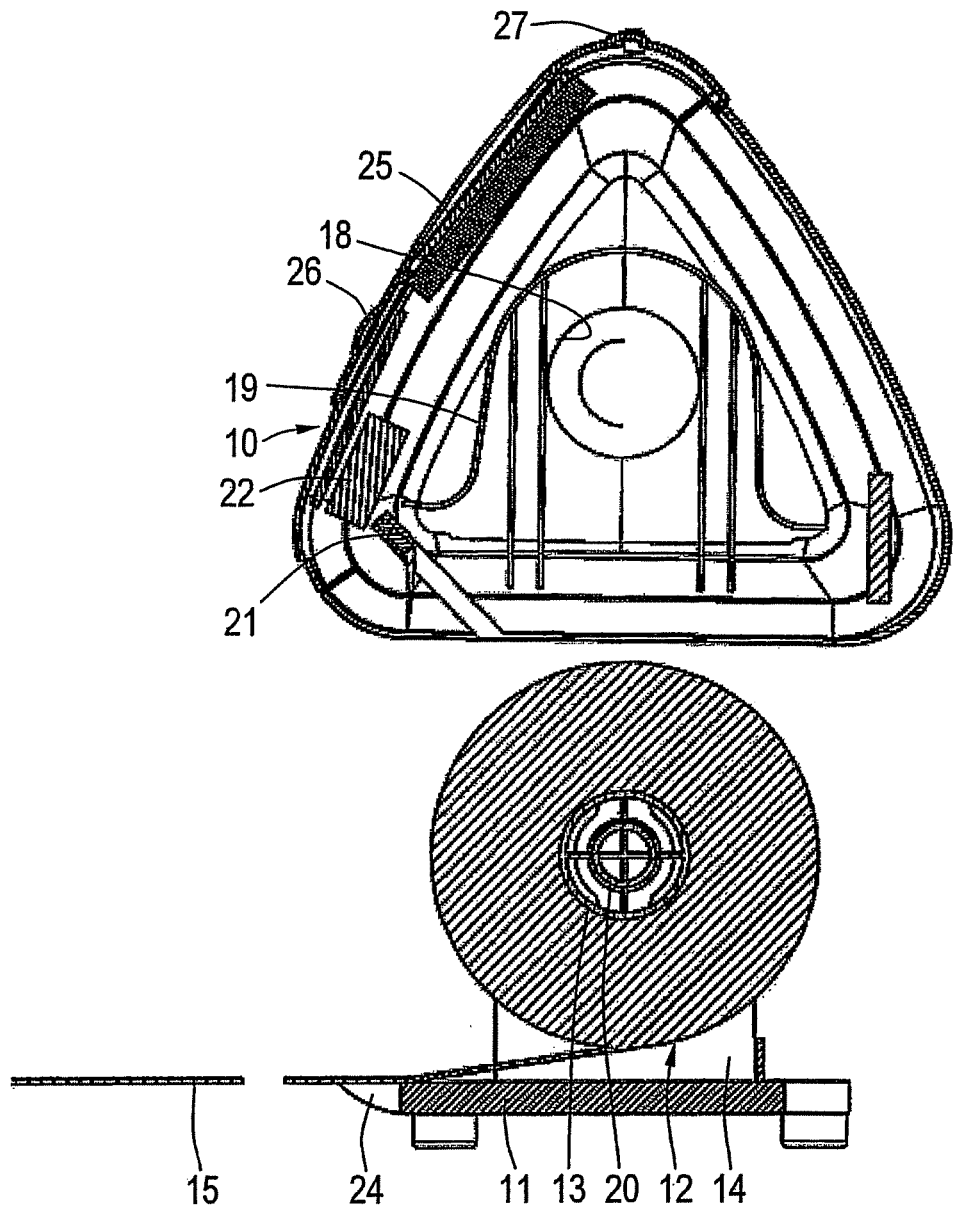
FIG. 5 is a sectional view along the line V-V in FIG. 2.
Figure 6:
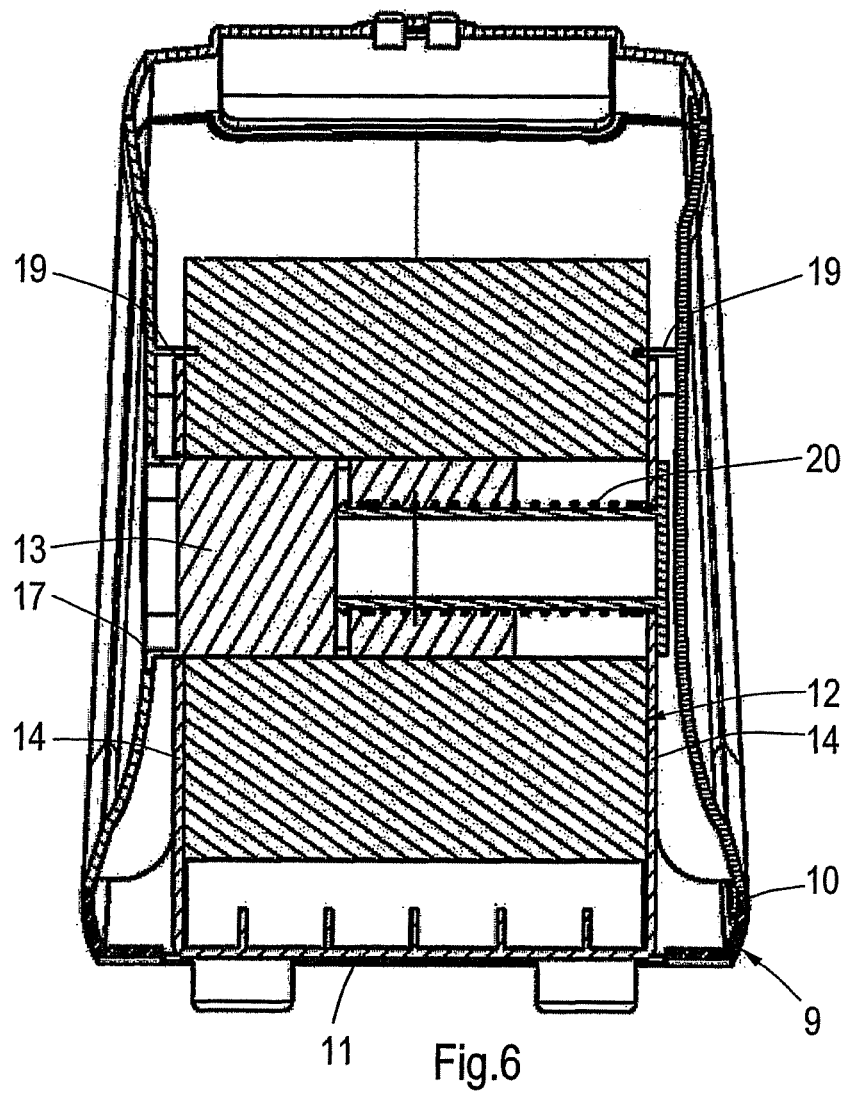
FIG. 6 is a sectional view along the line VI-VI in FIG. 3.

FIG. 1 illustrates the elements forming the system for assisting a patient in complying with a medical regimen. The heart of the system is formed by a dispensing device 1 which can be a stationary system used by the patient P, for example at home. The system further includes doctor(s) 2 who prescribe regimen(s) to the patient and is/are available for feedback and further assistance. A pharmacy 3 processes the prescription(s) of the medicine(s) by the doctor(s) and determines the final regimen for the next period to be followed by the patient P. A filling or packing station 4, which may be situated either at the pharmacy or in a separate place, packages the medicines in a plurality of portions. The complete package, including the plurality of portions, contains medicines for a certain period, for example a week, and is to be loaded in the dispensing device 1. The packing station 4 includes a data base 5 with the data of each of the regimes. The data of the regimen may be provided on the medicine package in a manner such that it can be read by the patient as well as by a reading member or device of the dispensing device 1. The data belonging to the regimen may for example be provided on the package in the form of one or more barcodes, RFID chips or other readable elements as is known in the art, and in text to allow for verification of the contents at all times.

A service center 6 is at the heart of a telecommunication network 7 and is in this embodiment able to communicate with the doctor(s) 2 and the dispensing device 1 and patient P. This latter communication is effected for example by a GPRS or GSM-phone or the like, which can either be the phone of the patient or can be a mobile phone unit built in the dispensing device 1. It is of course also possible that for example the dispensing device 1 communicates with the phone 8 of the patient through a blue tooth connection or the like. In this system also the filling station 4, in particular the database 5 thereof, is able to send information to the service center and to the dispensing device 1 in order to load the dispensing device 1 with information about the regimen and/or medicine(s) to be taken in the regimen. This information can be the same or is in addition to or to replaces (a part of) the information on the medicine package. The arrows in the communication network 7 in FIG. 1 provide an indication how communication may take place within the network. As an example, the system can operate as follows:

First of all, the doctor(s) in the doctor's post(s) 2 provide the patient P with prescription(s) based on the disease(s) they discovered with the patient. The prescription(s) are provided to the pharmacy, such as but not limited to the patient delivering the prescription(s) to the pharmacy 3. The pharmacy 3 determines the regimen based on the prescription(s) and on other available information about the patient, for example other medicines which are already used by the patient. The information about the regimen is then transferred to the database 5 of the filling station 4, and the packages are individually filled and as a set connected on a holding element. The holding element with the medicine package or packages are then delivered to the patient P through the pharmacy 3 and the patient or the pharmacy loads the dispensing device 1 with the holding element/package which contains medicines, such as pills, powders or the like for a certain period of time. The database 5 of the filling station also delivers information about the regimen to the dispensing device 1 either through the medicine package and/or through the telecommunication network. It also sends information about the regimen to the service center 6 so that the service center 6 is aware of the regimen of the patient P. The service center 6 could also send the information to the patients dispensing device 1, or another device such as his (mobile) phone, which then sends it to the dispensing device 1.

The dispensing device 1 reminds or warns the patient P when it is time to take the medicine(s) and if the patient P does not take the medicine within a certain time period, the dispensing device warns the service center 6. The service center 6 then tries to contact the patient P, for example, through his (mobile) phone 8, and/or might also warn the doctor's post 2 when the situation caused by not taking the medicine might become critical. The doctor 2 or his office may then also try to contact the patient P to advise the patient of the situation. The service center 6 may operate fully automatically or through an operator working there.

FIG. 1 shows that the system may also include a medical measuring device 30, such as a weighing device, but other electronic devices are conceivable such as a sphygmomanometer, tachycardia meter, coagulation factor meter, which is able to measure or monitor the effect of the medical therapy of the patient. The measuring device can be connected or connectable, for example but not limited to use of a Bluetooth connection, to the dispensing device 1. The dispensing device 1 is adapted to receive the data and to interpret this data in order to show it to the patient, for example through a display such as by means of graphs or other information with or without graphics. If the dispensing device 1 is loaded, for example through the service center 6, with data regarding the expected/desired effects of the therapy (which may be different for every patient), the patient is able to get feedback on the therapy. For example, the comparison value may be a certain range within which the measurements should fall (for example the coagulation factor), or may show a certain development in time how the measurements should progress (for example a decrease in blood pressure when using certain medicines or a particular decrease in weight when using other medication). The dispensing device may also be adapted to transfer the data through the communication network to the service center 6, so that the service center or the doctor communicating with it, is able to monitor the therapy from a distance. The dispensing device 1 may also transfer a warning signal if the measurements exceed certain values, so that the service center can take action if necessary.

FIGS. 2-10 illustrate embodiments of the dispensing device 1 as shown in FIG. 1, but it should be borne in mind that the dispensing device 1 could also be used in alternative systems.

The embodiment as shown comprises a housing 9 including a first housing part, in this case upper housing part 10, and a second housing part, in this case the bottom 11. The bottom 11 of the housing 9 is integrated or supports a holding element for a medicine package 12. The holding element in this case is a spindle 13 which is connected to the bottom 11 of the housing 9 through two vertical support webs 14.

The medicine package 12 in this embodiment is a strip of medicine bags 15 which are connected one to another in a way that they can be easily separated from each other, for example through a tear line or other preconfigured separation positions. In one embodiment, the medicine package 12 is pre-wound at the packing station on the spindle 13 of the holding element and is delivered to the patient as a unit with the holding element, such that the patient P (or the person at the pharmacy 3) only has to join the upper housing part 10 with the holding element bottom 11 in order to bring the spindle 13 with the dispensing device 1 in an operating condition. This is also caused by the fact that the bottom 11 has a portion which, in the assembled condition of the dispensing device 1 is adjacent an outlet opening 16 (see FIG. 3) of the device so that the first bag, containing all regimen info is by this design positioned in front of the electronic reading device and protrudes from said outlet opening 16 of the device in a position where it is within direct reach for the user to pull it forward out of the device. Consequently, the first or next medicine bag 15 projects from the bottom 11. It is therefore not necessary to thread the medicine package 12 through an opening or to exactly position it through the nip between rollers or the like, which makes it very easy for the patient to put the holding element with medicines and the dispensing device 1 together, reducing handling and failure risks.

In the embodiment illustrated, one side of the spindle 13 is configured as a pushbutton 17 which is adapted to click into an opening 18 in the upper housing part 10 in order to attach the spindle 13 to the upper housing part 10. The supporting webs 14, in particular the upper walls thereof, which are semicircular and the axis of curvature of which coincides with the axis of the spindle 13, co-operate with supporting ribs 19 on opposite inner walls of the upper housing part 10. These ribs 19 have an upper portion which is equal to that of the upper side of the supporting webs 14 and the lower portions are slightly diverging to facilitate introduction of the holding element into the upper housing part 10 and in particular to guide the supporting webs 14 and the pushbutton 17 to the correct position. Thanks to the single sided connection between the spindle 13 and the upper housing part 10 it is very easy to remove the holding element and the bottom 11 from the upper housing part 10 again because all elements are well within reach for the hands and the user can also move the holding element in the desired direction manually. Though 2 buttons on either side would seem logical, this would lead to a rather inconvenient procedure even with two hands. It is therefore avoided in this design to operate two pushbuttons on either end of the spindle 13. FIG. 4 shows the holding element with the spindle 13 and a helical spring 20 acting on the pushbutton 17 to load it to its outer position in which it locks the holding element in bottom 11 to the upper housing part 10.

Figure 7:
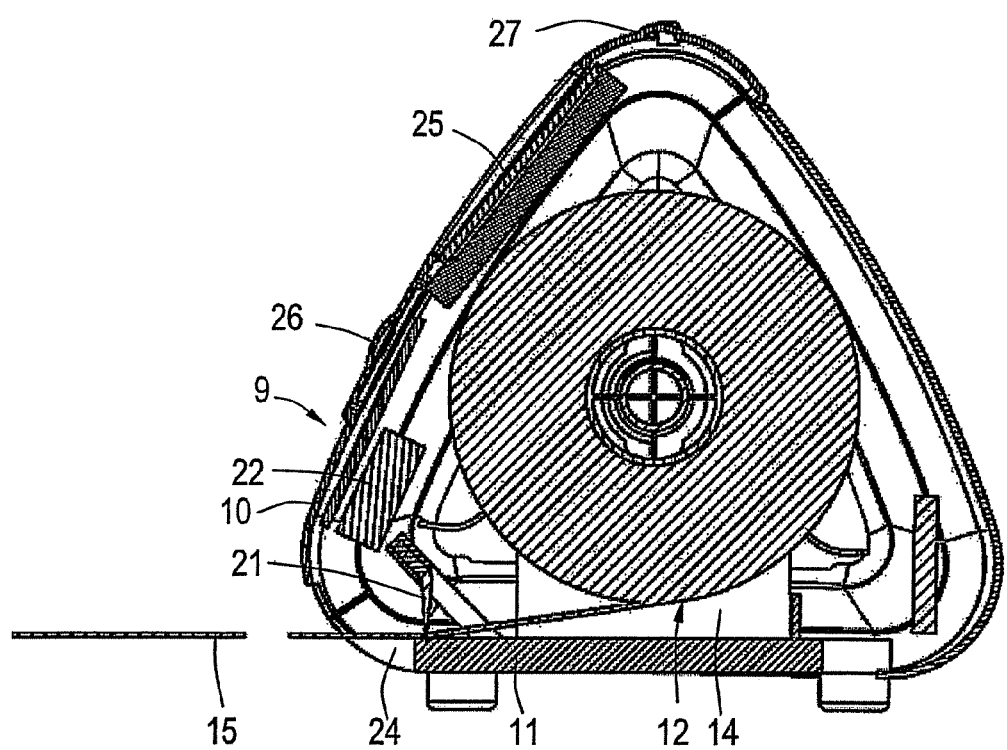
FIG. 7 is a sectional view corresponding to that of FIG. 5, but in a mounted condition of the device and on a larger scale.

FIG. 7 shows a flexible positioning member 21, which in this case is a rubber flap extending downwards until it lightly touches the upper side of the bottom 11 at a position inwardly of the outlet opening 16. As a result it flattens the respective bag 15 of the medicine package 12. The function thereof is to enable a reading device such as a barcode reader 22 attached to the upper housing part 10 to accurately read a barcode 15A on the medicine bag 15 whose front end is adjacent the outlet opening 16. This barcode 15A or any other information carrier may be present on the first (empty) bag to provide information on the complete medication package and the accompanying regimen and on each medicine bag 15 to enable the dispensing device 1 to get information about the contents of this specific medicine bag 15. However, it would also be possible that information about the medicine package 12 is only provided at the beginning of the medicine package 12 while the strip of the medicine package 12 is provided with a counting code, for example on one of its sides, enabling the dispensing device to count the bags 15 already dispensed, so that it is known which of the bags 15 is to be dispensed next.

The bottom 11 of the housing 9 is provided with a recess 11A adjacent the outlet opening 16 so that the patient can grip the front end of a medicine bag 15 which is present adjacent the outlet opening 16 in order to be pulled out. In order to enable a patient to wind the package 12 back on the spindle 13 if the package is pulled out too far, the spindle 13 is provided with finger grips 23 to enable the patient to rotate the spindle 13 in its winding direction. This manual transportation of the medicine package 12 keeps the dispensing device simple, although it is of course conceivable that the dispensing device 1 is provided with a motor in order to rotate the spindle 13 in a motorised manner to bring the next medicine bag 15 out to the exact correct position to tear it off.

Figure 8:
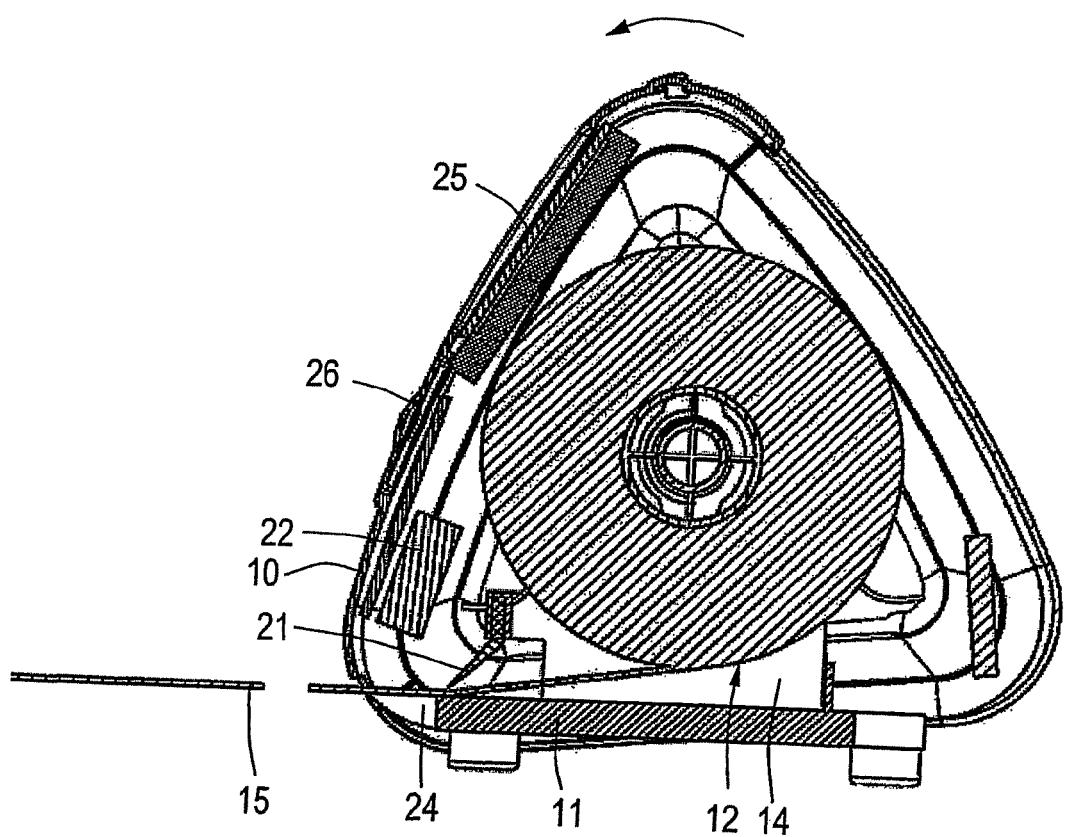
FIG. 8 is a view corresponding to that of FIG. 7, but showing a second embodiment with the medicine roll mounted and in a clamping position of the upper housing part.
Figure 9:
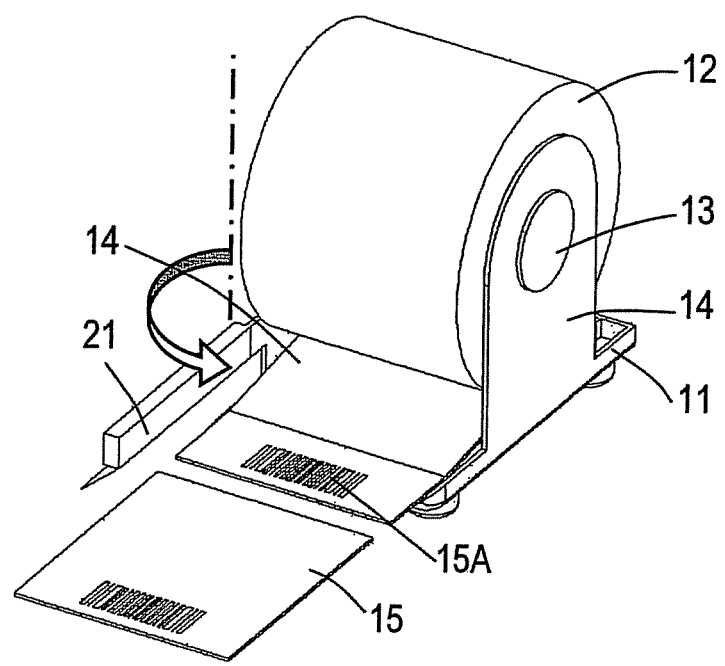
FIGS. 9 and 10 are perspective views of the holding element and medicine roll on the second embodiment of the device of FIG. 8 in two different positions.
Figure 10:
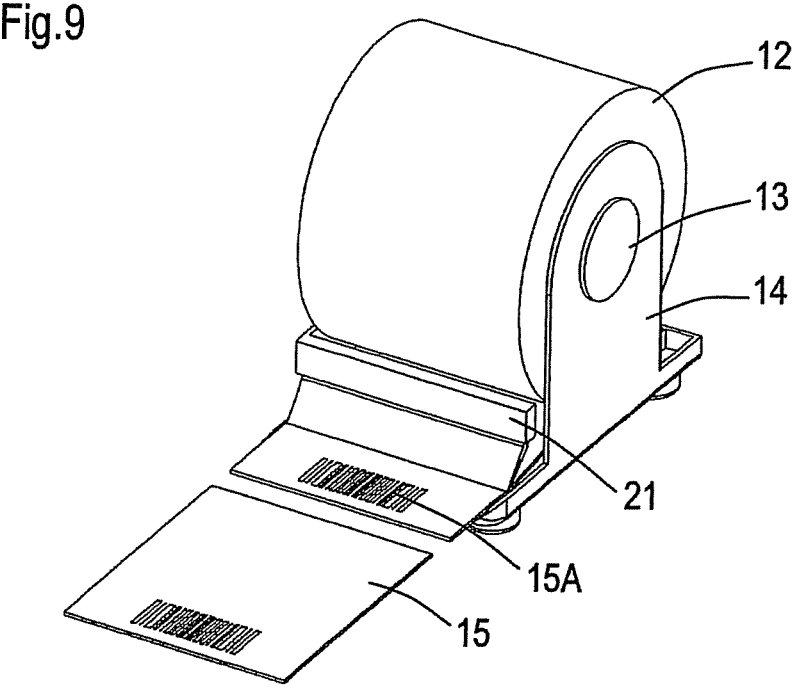

FIGS. 8-10 show a slightly modified embodiment, in which the positioning member 21 is not mounted on the upper housing part 10, but on one of the support webs 14 of the bottom 11 of the housing 9. FIGS. 9 and 10 show that this positioning member 21 can be mounted to one of the support webs 14 in a manner pivotable about a vertical axis in order to be rotated from an inoperable position according to FIG. 9 to an operable position according to FIG. 10.

FIG. 8 also illustrates that the upper housing part 10 is joined to the bottom 11 and spindle 13 such that it can be rotated with its end at the outlet opening 16 downwardly such that a clamping member 24 on the upper housing part 10 contacts the upper side of the bottom 11 with the medicine bag 15, in particular the front end thereof interposed in between. The clamping member will clamp the medicine bag inwardly adjacent the outlet opening 16. This enables the patient to tear off the medicine bag 15 projecting from the dispensing device 1 from the remainder of the medicine package 12. The movement of the clamping member of upper housing part 10 may also be used to switch on the reading member 22, so that it does not have to function continuously thereby saving energy from an energy source, such as a battery, although it is of course also possible to connect the dispensing device 1 to an outlet. During the movement of the upper housing part, the positioning member 21 will be moved downward in the embodiment of FIG. 7 to exert a higher pressure on the bag 15 and bottom 11 to further flatten the barcode 15A for its reading. From the above, it results that the upper housing part 10 is completely supported by the bottom 11, and is free from the underground so that it is free to move with respect to the bottom. A return member such as a spring could be used to bring the upper housing part 10 back to the non-clamping position.

If the upper housing part 10 would not be movable, a separate (sliding) clamping member could be provided on the upper housing part 10 near the outlet opening 16 in order to be able to clamp the medicine package 12 to assist in separating one or more medicine bags.

The dispensing device further comprises a display 25 to show information to the patient and to communicate with him or her. It may for example display: the name of the patient, which is system-linked to the GSM/GPRS phone in the unit or to the regular phone number of the user, information and instructions related to the regimen, a confirmation that the medicines have been taken correctly, the time of and/or the time to the next medicine taking, the actual date and time which are provided by the service center, next actions, an indication of the supply of medicines within the device, for example trough the number of days left, a score for the compliance to the regimen, patient name, battery status and the like. The display may also show instructions to the patient, for example: the manner of taking the medicines, what to do when the patient forgot to take a medicine portion, reminding the patient of a visit to the doctor, reminding a patient of obtaining a new medicine package and other instructions.

The electronics in the dispensing device is also capable to register particular information, such as the time a medicine bag is separated, the number of bags that have been separated, information about the medicine package inserted in the dispensing device, for example the name of the user, the period of time for which the medicine package is intended, the take in times, the names of the medicines, and any instructions accompanying the medicine package. The communication possibilities of the dispensing device may for example include: an anamnesis once a week, a signal to the service center when a risky situation might arise, a warning signal to the doctor, preferably through the service center in case of a need for assistance. In case the patient takes out more than one medicine bag 15 from the dispensing device, the dispensing device will check if this is done by accident or on purpose and it is programmed for the latter case in such a way that a reminder or warning signal is sent to the mobile phone of the patient, so the dispensing device is also able to remind or warn the patient from a distance. This enables the patient to follow his regimen even while being away from the dispensing device and it enables the device to keep track of the patients compliance whether he is present around the device or away from it. Of course, it would also be possible to have the dispensing device instruct the service center to remind the patient in case he is away from the dispensing device. This compliance "at a distance" can be registered by the device through the communication network instead of through direct operation of the dispensing device by the patient.

The dispensing device 1 can also comprise one or more operating buttons 26 for operating the device and communicating with it. The dispensing device reminds or warns the patient that medicines should be taken in by means of visual and/or acoustical signals or the like. The dispensing device as shown has LED lamps 27 which may be used to warn or remind the patient.

From the foregoing it will be clear that the invention provides a method, system and dispensing device for assisting a patient in complying with a medical regimen which is making life more easy for the patient and provides an intuitively understandable, and easy to operate device.

The invention is not limited to the embodiments shown and described hereinbefore which may be varied in different ways within the scope of the invention. For example, the medicine package may be of a different design, such as a blister strip or a strip containing other medicine containers. The package could be supplied separately, so that the pharmacy or the patient should bring the package into or onto the holding element of the dispensing device. The holding element for the medicine package may also include a part that protrudes through a wall, in particular a bottom of the housing in stead of being provided with a part of the housing, in particular a wall part of the housing. It may define one side of the outlet opening but may also define the complete opening. Alternatively, it may stop inwardly of the outlet opening, in particularly if there is a mechanism getting the first end of the medicine package through the outlet opening.

The invention claimed is:

1. A system for assisting a patient in complying with a medical regimen having a plurality of medicines, comprising:
    a package having a plurality of containers, each container having a portion of each of the plurality of medicines, the package comprising machine-readable information about the regimen, wherein the package comprises a strip containing the plurality of containers, and wherein the dispensing device includes a housing, a holding element within the housing to take up the strip of containers, an assisting device that engages the strip to separate one or more containers from the strip adjacent an outlet opening of the housing, and wherein the holding element is mounted to a part of the housing adjacent the outlet opening, and wherein the strip of medicine containers, the holding element and the part of the housing are exchangeable as a unit;
    an electronic dispensing device to be used by the patient which stores the package and dispenses separately each of the plurality of containers within the package and comprises electronics, wherein the electronics register operation of the dispensing device by the patient to take medicine, and wherein the electronics includes a reading element that reads the information about the regimen on the package and a warning device that outputs a signal at least on the basis of the machine-readable information on the package;
    a service center; and
    a communicating network that is operably connected to the service center and the dispensing device and communicates information between the dispensing device and the service center, wherein the service center includes information about the regimen, and wherein the dispensing device and the service center communicate information about the regimen.

2. The system according to claim 1, wherein the dispensing device is provided with a telephone module and wherein the communication network is a wireless telecommunication network.

3. The system according to claim 1, wherein the holding element is a spindle on which the strip of containers are prewound, the spindle having a drive to wind and/or unwind the strip of containers.

4. The system according to claim 3, wherein the drive for the spindle is a gripping part connected to the spindle to manually rotate the spindle.

5. The system according to claim 1, wherein the part of the housing is a bottom of the housing, or protrudes through a bottom of the housing.

6. The system according to claim 1, wherein the assisting device is a clamping member adjacent the outlet opening for the containers in order to clamp the strip of containers adjacent a position where one or more containers are to be separated.

7. The system according to claim 6, wherein the reading element is activated by an element that is coupled to the clamping member.

8. The system according to claim 1, wherein the part of the housing and a remaining part of the housing are movable with respect to each other, the clamping member being coupled to one of the part of the housing or the remaining part of the housing and cooperating with the other part of the housing to clamp the strip of containers.

9. The system according to claim 8, wherein the clamping member is attached to an upper part of the housing and cooperates with a bottom of the housing, the bottom of the housing supporting the holding element.

10. The system according to claim 9, wherein the upper part of the housing is pivotable with respect to the bottom of the housing, and wherein the bottom of the housing includes a support member supporting the upper housing part in a pivotal manner.

11. The system according to claim 10, wherein the holding element is a spindle and the support member for the upper housing part also supports the spindle, the bottom of the housing being configured to connect to the upper housing part through a push button on one end of the spindle.

12. The system according to claim 1, wherein the dispensing device includes a flattening member that positions the strip adjacent the reading element.

13. The system according to claim 1 and further comprising a medicine packing station packing connected to the communicating network, the medicine packing station packing said containers within the according to the regimen.

14. The system according to claim 1 and further comprising a database connected to the communicating network storing information about the regimen.

* * * * *